(12) United States Patent
Buckner et al.

(10) Patent No.: US 9,232,117 B2
(45) Date of Patent: Jan. 5, 2016

(54) DIGITAL SCHLIEREN IMAGING

(71) Applicants: Benjamin D. Buckner, Irvine, CA (US); Drew L'Esperance, Irvine, CA (US)

(72) Inventors: Benjamin D. Buckner, Irvine, CA (US); Drew L'Esperance, Irvine, CA (US)

(73) Assignee: MetroLaser, Inc., Laguna Hills, CA (US)

( * ) Notice: Subject to any disclaimer, the term of this patent is extended or adjusted under 35 U.S.C. 154(b) by 248 days.

(21) Appl. No.: 13/796,237

(22) Filed: Mar. 12, 2013

(65) Prior Publication Data

US 2014/0267781 A1    Sep. 18, 2014

(51) Int. Cl.
| | |
|---|---|
| H04N 9/083 | (2006.01) |
| H04N 5/225 | (2006.01) |
| H04N 5/21  | (2006.01) |
| G01N 21/45 | (2006.01) |

(52) U.S. Cl.
CPC . *H04N 5/21* (2013.01); *G01N 21/45* (2013.01)

(58) Field of Classification Search
None
See application file for complete search history.

(56) References Cited

U.S. PATENT DOCUMENTS

| | | | |
|---|---|---|---|
| 2,642,770 A  |   | 6/1953 | Zobel |
| 3,617,130 A  |   | 11/1971 | Kelley et al. |
| 3,847,484 A  |   | 11/1974 | Gropper et al. |
| 4,139,291 A  | * | 2/1979 | Frosch et al. ............... 396/431 |
| 4,812,039 A  |   | 3/1989 | Shimada et al. |
| 4,998,207 A  | * | 3/1991 | Postlewait ................... 700/166 |
| 5,515,158 A  |   | 5/1996 | Heineck |
| 5,896,170 A  | * | 4/1999 | Webb et al. .................. 348/190 |
| 6,538,691 B1 | * | 3/2003 | Macy et al. ................ 348/222.1 |
| 7,206,079 B2 |   | 4/2007 | Joannes |
| 7,580,559 B2 |   | 8/2009 | Latypov et al. |
| 2003/0043458 A1 | * | 3/2003 | Minobe et al. .............. 359/386 |
| 2007/0286514 A1 | * | 12/2007 | Brown et al. ............... 382/254 |
| 2008/0013050 A1 | * | 1/2008 | Boute et al. ................. 353/10 |
| 2008/0117438 A1 | * | 5/2008 | Quirion et al. ............. 356/610 |
| 2011/0063268 A1 | * | 3/2011 | Knapp ........................ 345/207 |
| 2012/0113430 A1 | * | 5/2012 | Liu et al. .................... 356/456 |
| 2013/0002932 A1 | * | 1/2013 | Guenter et al. ............. 348/345 |
| 2014/0300869 A1 | * | 10/2014 | Hirsch et al. ............... 353/7 |

OTHER PUBLICATIONS

University of the Witwatersrand, "Improvements on Schlieren Systems (Schlieren Imaging Systems)", P16514ZA00/LP, Nov. 27, 2007, pp. 13, Johannesburg, South Africa.
Burton, R.A., "A Modified Schlieren Apparatus for Large Areas of Field," J. Opt. Soc. Am. 39, 907-907 (1949).

* cited by examiner

*Primary Examiner* — Aung S Moe
*Assistant Examiner* — Euel Cowan
(74) *Attorney, Agent, or Firm* — Haynes and Boone, LLP

(57) ABSTRACT

A Schlieren imaging system can comprise a digital display configured to provide a background for Schlieren imaging, a cutoff filter onto which the background is focused, and a camera configured to image the cutoff filter and the background to facilitate Schlieren imaging. A calibration method for the Schlieren imaging system can comprise forming a pixel image on a digital display, focusing the pixel image on the cutoff filter, imaging the cutoff filter and the pixel image with a camera; and moving the pixel image with respect to the cutoff filter to align the pixel image with respect to the cutoff filter to facilitate Schlieren imaging. Thus, alignment of the Schlieren imaging system can be substantially simplified.

24 Claims, 3 Drawing Sheets

DIGITAL SCHLIEREN IMAGING

TECHNICAL FIELD

The present invention relates generally to optics. The present invention relates more particularly, for example, to methods and systems for enhanced Schlieren imaging.

BACKGROUND

Schlieren imaging is well known. Schlieren imaging is a technique for visualizing wavefront distortions or "phase objects" in transparent media. Schlieren imaging can be used to characterize such physical parameters as temperature, density, and pressure. As those skilled in the art will appreciate, such parameters are important in aerodynamics, fluid dynamics, and various other branches of engineering. Schlieren imaging facilitates the formation of an image using light rays that pass by a sharp cutoff filter. The filter is arranged so that the ray intensity has a steep derivative along the edge of the filter. This arrangement allows small deviations in the path of the light rays to produce a large change in the intensity of an image with respect to the intensity of the image caused by undeviated light rays.

Classical Schlieren systems use light collimated by optics such as mirrors or lenses. The use of such optics substantially limits the area under test to approximately the size of the optics. An important improvement with respect to the original Schlieren concept is the complementary-grid focusing Schlieren system. The complementary-grid focusing Schlieren system uses the same edge filtering. However, instead of using collimated light, the complementary-grid focusing Schlieren system images a background grid pattern onto a complementary opaque cutoff filter such that the cutoff filter edges lie along the edges of the background grid pattern. The target object is imaged in a different plane with respect to the cutoff filter, as facilitated by the camera objective. The focusing approach generally allows for obtaining Schlieren imaging through much larger areas without using excessively large optics. Such techniques thus generally require less expensive equipment as compared to classical collimated-light Schlieren systems and can more easily be scaled up to cover large areas. However, such techniques tend to be more difficult to set up and align as compared to classical collimated-light Schlieren systems.

BRIEF DESCRIPTION OF THE DRAWINGS

Embodiments of the present invention and their advantages are best understood by referring to the detailed description that follows. It should be appreciated that like reference numerals are used to identify like elements illustrated in one or more of the figures.

DETAILED DESCRIPTION

Figure 1:
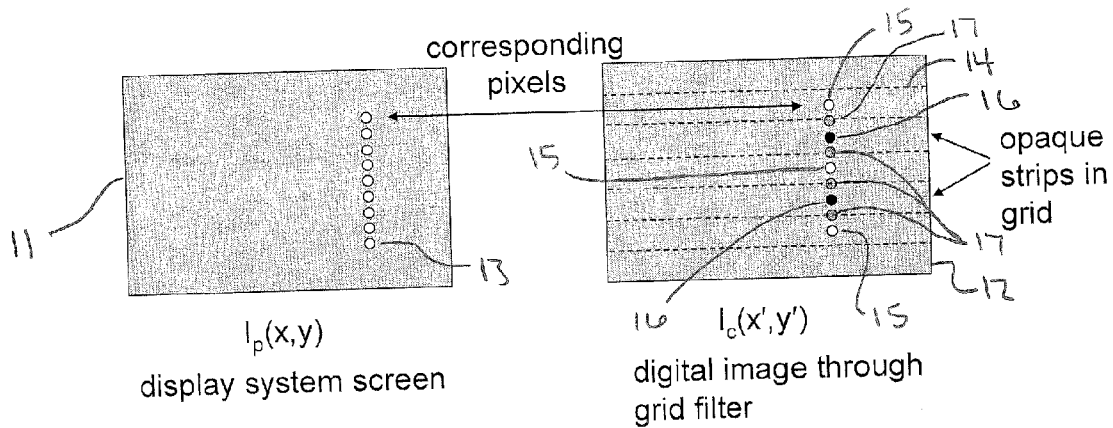
FIG. 1 is a diagram showing a calibration procedure, according to an example of an embodiment.

As discussed above, the complementary-grid focusing Schlieren system uses the same edge filtering as classical collimated-light Schlieren systems and instead of using collimated light, uses a background grid pattern imaged onto a complementary opaque cutoff filter, e.g., a grid, a cutoff grid, screen grid, or spatial filter, such that the filter edges lie along the edges of the background grid pattern. This focusing approach generally allows for obtaining Schlieren imaging through much larger areas without using excessively large optics. However, such techniques tend to be more difficult to set up and align as compared to classical collimated-light Schlieren systems.

According to an embodiment, such difficulties with setting up and aligning a contemporary Schlieren imaging system are substantially mitigated. More particularly, a system and method can substantially reduce the cost and complexity of a focusing Schlieren imaging system. For example, one difficulty with the contemporary focusing Schlieren systems is that the cutoff grid and the background grid have to be very precisely matched to one another in order to obtain good sensitivity. This alignment requirement makes the system very sensitive to misalignment and aberrations in the optical system.

According to an embodiment, an optomechanically simplified Schlieren receiver apparatus can be provided. The simplified Schlieren apparatus can comprise a display device, such as a digital display. For example, the digital display can be a computer monitor, a television, a digital projector, or the like that is configured to provide the background, e.g., the grid pattern. The digital display can be a liquid crystal device (LCD), a light emitting diode (LED) device, a plasma device, or any other suitable device.

The display device can be used to provide, either directly or indirectly, a background grid pattern. The display device can be used directly to provide the background grid pattern by displaying the background grid pattern on the display device while making the display device the background. The display device can be used indirectly to provide the background grid pattern by using the display device to project a displayed image of the background grid pattern upon the background, e.g., a projection screen. Thus, the display device can define, at least in part, a projector.

According to an embodiment, the display device can be controlled by a computer. Thus, the background grid pattern can be produced by a computer controlled display device. Such control facilitates substantially precise matching or aligning of the background to the Schlieren cutoff filter. That is, the image displayed upon the display device can be moved precisely to accomplish such alignment. For example, the image displayed upon the display device can be moved one pixel at a time to precisely accomplish such alignment.

The Schlieren cutoff filter can be either analog or digital. A software based calibration process can facilitate such matching. The software based calibration process can facilitate such precise, e.g., pixel based, alignment. For example, the background can be aligned with respect to the cutoff filter with an accuracy of one pixel or less than one pixel of the display device. The alignment can be performed electronically, without the need to physically move the background or the cutoff filter. According to an embodiment, the image of the background and/or the image of the cutoff filter move to facilitate alignment.

The display device or projector and the digital camera receiving the image can both be controlled by the computer. Control software on the computer can measure the point spread function (PSF) of the display device or projector through the optical system and the cutoff filter by modulating individual pixels and analyzing the response measured with the digital camera.

According to an embodiment, a calibration procedure can facilitate alignment of the optomechanically simplified Schlieren receiver apparatus. The calibration procedure can be a software controlled alignment process that makes the Schlieren system substantially less expensive to manufacture and easier to set up.

Separating the passive Schlieren receiver module from the image generation components also allows the use of highly engineered, commercially available display and projection systems, thus reducing the system cost while potentially enhancing portability and flexibility. The software can correct for optical aberrations via the calibration process. In this manner, aberration compensation and alignment advantages can be provided at the same time, e.g., via the same procedure.

Embodiments can be provided with either a projector or a self-illuminating display device. The self-illuminating display device typically operates in a single pass mode, where the rays pass through the flow once before being detected.

The projector display device can operate either in a single pass or double pass configuration. The single pass mode of operation has advantages in some Schlieren applications, such as when the object is viewed through a window where stray reflections off of the window surface can overwhelm the image. The double-pass projector approach can yield higher sensitivity because a given distortion can be passed twice by the same ray, doubling the deviation.

Because digital projection systems and computer display devices generally use the same interface protocols, point spread function calculation software can be essentially identical in either embodiment. The same Schlieren receiver module can be used with either embodiment of the invention. The double pass projection version requires the addition of a beam splitter and a mount, as well as a rough mechanical alignment. A mounting bracket can be provided to attach the Schlieren module rigidly to a projector.

The point spread function calibration procedure can take many possible forms. According to embodiments, the edges of the cutoff filter as they project into the screen plane can be mapped, pixels corresponding to the occluded parts of the cutoff filter can be brightened, and/or pixels which correspond to the transparent parts of the cutoff filter can be darkened. An enhanced Schlieren image can be formed when the detail of the grid pattern is fine enough that the image of the grid blurs into a smooth background when the foreground object is focused.

Generally, the grid of the cutoff filter can comprise an array of parallel transparent and opaque lines, such as a Ronchi ruling. The refractive index gradient which is perpendicular to the lines produces the strongest Schlieren effect. However, other grid patterns may be used to tune the system for sensitivity to different gradient directions. For example, a cutoff grid of opaque squares could be used with projected lines to produce a coarser, less sensitive Schlieren image, but with the advantage that the direction of the projected lines can be switched in software to change the gradient direction sensitivity. Also, radial grid patterns can be used to detect radial refractive index gradients of the target.

Any desired pattern or combination of patterns can be used for the background and/or the cutoff filter. The grid pattern can be optimized with respect to known or suspected refractive index gradients of the target. A custom grid can comprise such optimized grid patterns.

An electronically controlled transparency, such as a liquid crystal display, can be used for the cutoff grid. The electronically controlled transparency can be used to perform higher sensitivity collimated-light Schlieren measurements. The use of either a controllable cutoff filter or a controllable background grid image provides substantially the same capability. However, having both a controllable cutoff filter and a controllable background provides the ability to arbitrarily adjust the Schlieren directional sensitivity at substantially the update speed of the control systems. For example, both the background and the cutoff filter can be rotated to obtain approximately the orientation of greatest sensitivity.

Two dimensional Schlieren imaging can be achieved by alternating between horizontal and vertical stripes. Other, e.g., intermediate, angles can likewise be used. The sensitivity to particular features can also be dynamically adjusted by selecting grid angles that have maximum contrast. The system can accommodate various background grid angles and patterns, making the system extremely versatile and adaptable to a wide variety of applications without substantial added cost. The system can automatically image using various angles and patterns in an attempt to provide enhanced Schlieren imaging.

According to an embodiment, intermediate pixel intensity values can be used to compensate for partially occluded display pixels. Because the display resolution is inherently granular, the quality of the Schlieren image can be somewhat improved if intermediate pixel intensity values are used to compensate for partially occluded display pixels.

According to an embodiment, a device can comprise an electronic display, such as a digital display. The digital display can be configured to provide a background for Schlieren imaging. The background can be focused onto a cutoff filter. A camera can be configured to image the filter and the background to facilitate Schlieren imaging.

The background can be a pattern. The pattern can be complimentary to a pattern of the cutoff filter. For example, the background can be a plurality of vertical or horizontal stripes. The pattern can be any other desired pattern.

A direct image of the background can be focused upon the cutoff filter. Thus, the digital display itself (such as a screen of the digital display) can be focused upon the cutoff filter. For example, the screen of a light emitting diode (LED) or liquid crystal display (LED) can be focused upon the cutoff filter.

A projected image of the background can be focused upon the cutoff filter. Thus, the digital display can define or can be part of a projection system. The projection system can project the screen of the digital display, which can then be focused upon the cutoff filter.

The background can be complementary with respect to the cutoff filter. For example, the cutoff filter can comprise an array of vertical opaque and transparent stripes while the background can comprise a plurality of light (e.g., white) and dark (e.g., black) stripes.

A processor can be configured to control a position of the background to facilitate alignment of the background with respect to the cutoff filter. The processor can be a general purpose computer. For example, the processor can be a personal computer (PC). Thus, the background can be moved, shifted, translated, and/or rotated by the computer one pixel at a time to facilitate alignment. Mechanical adjustment, such as via a micrometer, stage, or the like, can optionally be provided for the digital display and/or the cutoff filter in any desired directions (including one, two, or three axes of translation and/or one, two, or three axes of rotation).

The digital display can comprise a light emitting diode (LED) display. The digital display can comprise a liquid crystal display (LCD). Any other type of display for which pixels can be moved to facilitate alignment of the Schlieren system can be used. Various types of electronic displays are contemplated.

The digital display can comprises a light source and an electronically controllable light transmissive screen. The electronically controllable light transmissive screen can be used for selectively allowing light from the light source to be transmitted therethrough. In this manner, a background pattern can be provided for calibration and/or Schlieren imaging.

According to an embodiment, a method can comprise forming a pixel image on a digital display. The pixel image can be focused on a cutoff filter. The cutoff filter and the pixel image can be captured or imaged with a camera. A position of the pixel image can be varied with respect to the cutoff filter to align the pixel image with respect to the cutoff filter to facilitate Schlieren imaging.

Varying a position of the pixel image with respect to the cutoff filter can comprise moving the pixel image. The pixel image can be moved in any manner or direction that facilitates alignment of the background with respect to the cutoff filter.

A point spread function of the pixel image can be mapped with respect to the cutoff filter. The point spread function of the display pixels can be mapped by displaying a single pixel and imaging the single pixel with the camera at a plurality of points in a display field. The point spread function of the display pixels can be mapped by displaying a plurality of pixels simultaneously and imaging the plurality of pixels with the camera.

A point spread function of each pixel can be inverted. The inverted point spread functions can be added together to provide a projection that is complementary to the cutoff filter. The Schlieren effect can be observed with the camera to facilitate alignment of the background with respect to the cutoff filter.

An output of the camera can be processed to provide a feedback signal. The feedback signal can be provided to the display device to generate an enhanced Schlieren background pattern. That is, the feedback signal can be used to move the background so as to enhance the alignment of the background with respect to the cutoff filter.

The digital display, the cutoff filter, and the camera can be part of a Schlieren imaging system that has optical aberrations. An analytical approximation to the optical aberrations can be estimated by projecting a plurality of calibration patterns to define a model. A Zernike polynomial representation and/or affine map can be estimated with respect to optical aberrations by projecting calibration patterns to define a model. The model can be to determine locations of a plurality of pixels for use in mapping a point spread function.

An approximately complimentary grid pattern for either the background with respect to the cutoff filter or for the cutoff filter with respect to the background can be generated without a prior calibration. The grid pattern can be matched an aberrated cutoff grid by an error minimization process.

An effective resolution of the digital display can be enhanced by processing different color components of each pixel separately. A Schlieren contrast can be enhanced by applying an exponential transformation relative to an intensity level without Schlieren contrast.

The cutoff filter can comprise a device with controllable transparency. Varying a position of the pixel image with respect to the cutoff filter can comprise moving a pattern of the cutoff filter.

The cutoff filter can comprise a device having controllable transparency. The cutoff filter can comprise either a controllable display such that a measured Schlieren gradient direction can be controlled dynamically.

The background can be provided by a time varying light source and a digital display having controllable transparency. The digital display can be configured to modulate light from the time varying light source.

According to an embodiment, a device can comprise a digital display configured to provide a background for Schlieren imaging. The background can be focused onto a cutoff filter. A camera can be configured to image the filter and the background to facilitate Schlieren imaging. The digital display can be configured to move a pixel image with respect to the cutoff filter to align the pixel image with respect to the cutoff filter.

FIG. 1 is a diagram showing a calibration procedure, according to an example of an embodiment. A display system screen 11 can define a background having a plurality of background pixels 13. The display system screen 11 can be a screen of a digital display, such as the digital display that provides the background for the digital Schlieren imaging system. The display system screen 11 can form pixel images 15-17 (that correspond to the pixels 13) on an imager or digital camera to define a digital image 12. The digital image 12 of the display system screen 11 can be taken through a cutoff filter.

Thus, the digital image 12 can contain the pixel images 15-17. Each background pixel 13 can correspond to one of the pixel images 15-17. Each background pixel 13 can either be directly displayed or projected by the display system, as disclosed herein. The background pixels 13 can be displayed either sequentially (such as one or more at a time) or simultaneously (all at the same time).

The illumination value of each displayed or projected background pixel $I_p(x,y)$ can be set to its maximum value and the response $I_c(x',y')$ can be measured using the digital camera with which the digital image 12 is formed. $I_c(x',y')$ can be the integrated intensity, as measured by the digital camera and which originates from the background pixel at (x,y). Because the image of a discrete display pixel may be blurred, it is usually necessary to integrate the image intensity around the point in the image (x',y') which corresponds to the display pixel location (x,y).

In normal operation, the display plane is not focused on the imager, in which case the area of the blur may be substantial. If the focus is set to the display plane for calibration, only a few image pixels may need to be integrated since the display is in focus. The smaller the integration area, the faster the calibration can proceed, because the pixels can be displayed in batches that are separated by the blur diameter. That is, if the blurred pixel images are sufficiently far apart, they can be distinguished and measured separately, so if the blur diameters are smaller, more pixels can be processed together in a single frame.

If large image distortions are present and not known exactly, the integration area may also need to be large in order to ensure that the pixel image is included within the integration area. The mapping of pixel locations from the display (x,y) coordinates to the image (x',y') coordinates can be determined by analyzing test images such as circles or a checkerboard pattern displayed on the display screen by software, according to pattern recognition methods which are well known in the art. In the case where optical distortions are low, this mapping can be well approximated by an affine transform from (x,y) to (x',y').

In locations in the image plane which are not blocked by the grid filter, pixels 13 will appear bright to define bright image pixels 15. In locations that are blocked by the grid filter, pixels 13 will appear dark to define dark pixels 16. Pixels 13 which lie on a boundary 14 have intermediate intensity levels to define intermediate pixels 17. The calibration procedure can illuminate each pixel on the display and measures the response with the camera, thereby creating a map of the grid filter edges relative to both the image and the display device coordinates.

Figure 2:
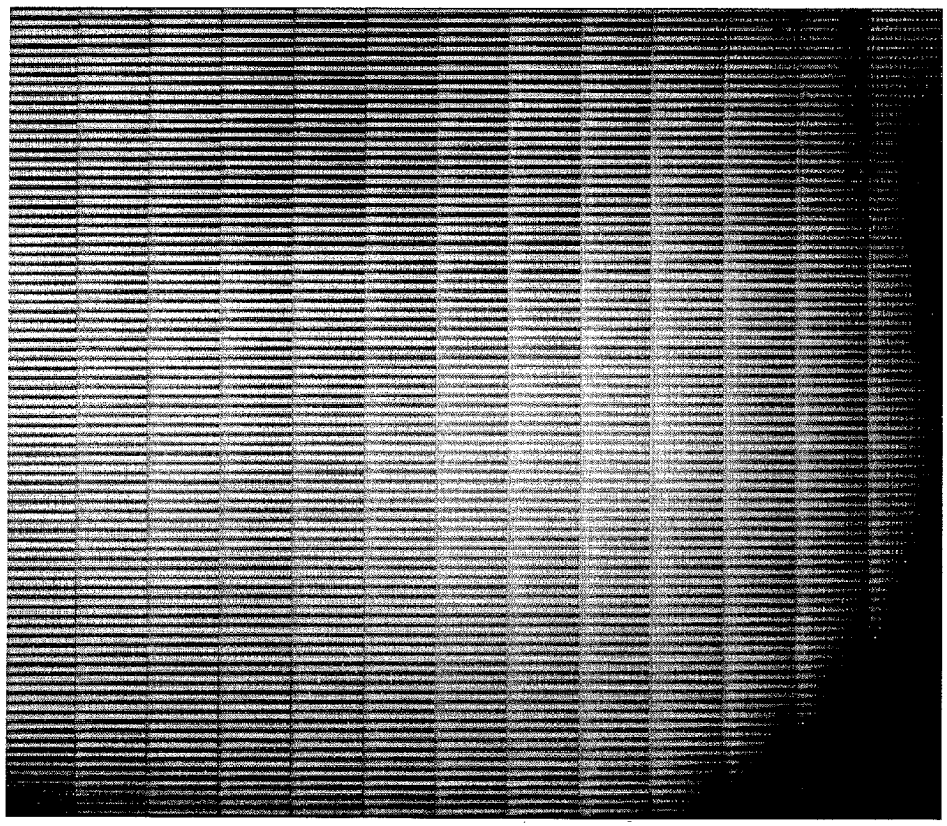
FIG. 2 shows a complementary background grid generated for an LCD display with a horizontal Ronchi cutoff grid, according to an example of an embodiment.

FIG. 2 shows a complementary grid generated for an LCD display with a horizontal Ronchi cutoff grid, according to an example of an embodiment. To maximize Schlieren sensitivity, the maximum ($I_{c,max}$) and minimum ($I_{c,min}$) values of $I_c(x',y')$ over the active Schlieren field can be found and used to scale each $I_c(x',y')$ to a relative value, $I_c'(x',y')=(Ic(x',y')-I_{c,min})/(I_{c,max}-I_{c,min})$.

The displayed grid pixel intensities can be scaled according to the display's dynamic range to maximize contrast, $I_p(x,y)=(1-I_c'(x',y'))(I_{p,max}-I_{p,min})$ where $I_{p,min}$ is zero in most practical cases. This procedure results in a complementary grid such as that shown in FIG. 2. This grid has its intensities balanced with the point spread function of the optical system and variations in display response so that the Schlieren background is smooth and even when imaged through the display system.

During calibration, the software may have to take "dead pixels" into account. For some displays, there are logical pixels which do not produce illumination, and these consequently do not produce a response $I_c'(x',y')$. These dead pixels should be excluded from the calculation of the minimum response value in order to obtain the greatest useful dynamic range from the Schlieren pattern.

Alternatively, a threshold for $I_c(x',y')$ can be used to determine whether to set $I_p(x,y)$ at its maximum or minimum value and inhomogeneities due to partially occluded pixels can be removed by background subtraction after each Schlieren image is acquired. This approach can give better sensitivity (Schlieren contrast) for display devices in which the physical intensity difference between the 0 and 1 logical intensity levels is larger than for other intensity increments, which is a feature sometimes designed into display systems for better viewing contrast. As those skilled in the art will appreciate, various image processing steps well known to the art can be applied to improve the point spread function analysis accuracy and speed.

The Schlieren background subtraction procedure is different with respect to the conventional background subtraction in that it must be a signed subtraction because Schlieren contrast can be positive or negative relative to the background. It can also be useful to apply gamma correction to the background difference to enhance weak Schlieren features relative to strong Schlieren features.

According to an embodiment, a device can use a digital display as a light source for producing Schlieren images. Software, firmware, computer instructions, or the like can be used to control the digital display to produce programmed images which can used to calibrate the displayed image to be complementary to the cutoff filter, as disclosed herein.

According to an embodiment, a device can use focusing Schlieren imaging. Thus, refractive index variations in a medium can be visualized or characterized based on imaging of a background pattern. The device can comprise a filter, imaging optics, camera, display device or projector, computing device, and software. The software can facilitate the production an image on the display device or projector which is complementary to the filter, thus allowing the spatial filter to act as a Schlieren cutoff filter.

Figure 3:
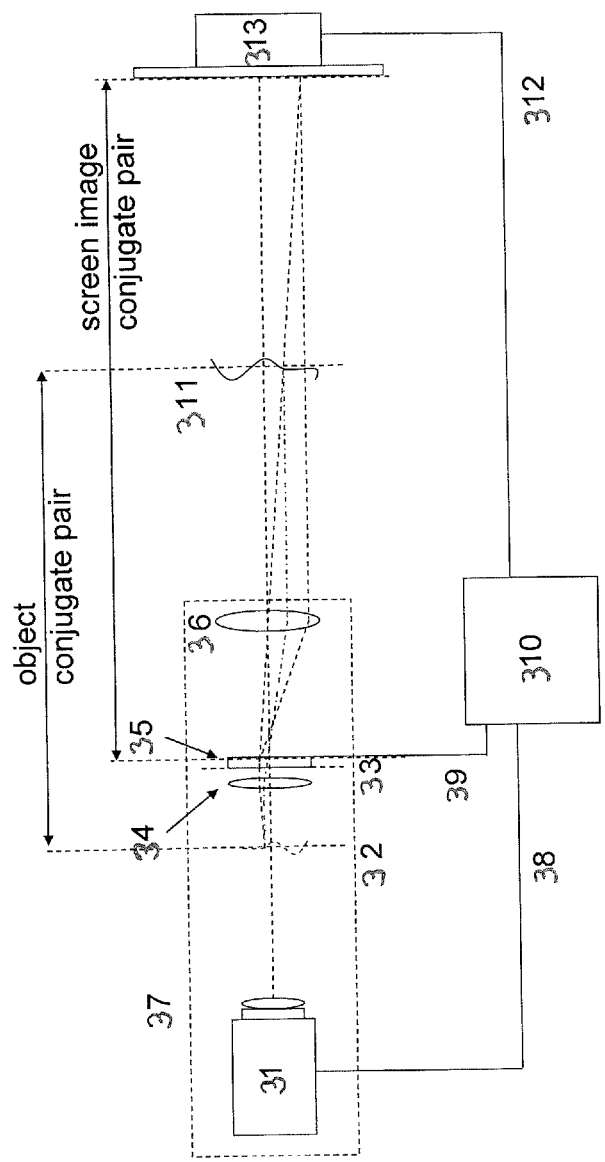
FIG. 3 is a block diagram of a direct display based Schlieren system, according to an example of an embodiment.
Figure 4:
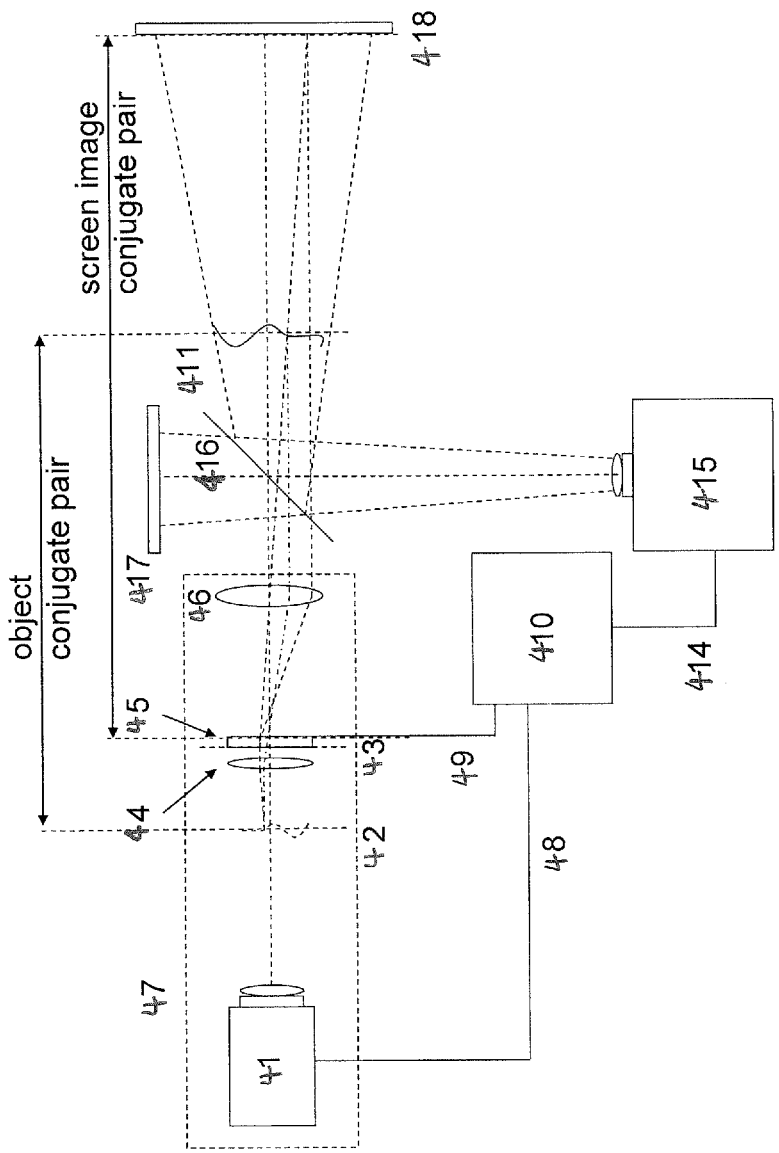
FIG. 4 is a block diagram of a projector based Schlieren system, according to an example of an embodiment.

Referring now to FIGS. 3 and 4, two different embodiments of the digital Schlieren imaging system are shown. According to one embodiment, the digital display can be a direct digital display, such as digital display 313 of FIG. 3 which is discussed in further detail below. According to another embodiment, the digital display can be a digital display projection, such as digital display projection 418 of FIG. 4, which is discussed in further detail below.

The background image provided by the digital display 313 or 415, whether it is a direct image (as provided by digital display 313) or a projected image (as provided by digital display 415), can define a background pattern. The background pattern can be imaged onto the cutoff filter 35 (FIG. 3) or 45 (FIG. 4) and an image from the filtered image plane 33 (FIG. 3) or 43 (FIG. 4) can be captured by a camera 31 (FIG. 3) or 41 (FIG. 4), either with the focus on the plane 33 or 43 for calibration or with the focus on a different plane to capture the image of an object of interest or target 311 (FIG. 3) or 411 (FIG. 4).

The software can facilitate precise matching of the background image with respect to the cutoff filter 35 or 45, thereby substantially reducing the cost, size, and complexity of the Schlieren system relative to contemporary systems. According to one or more embodiments, the digital display or projection system can consist of inexpensive commercial devices such as computer monitors or digital projectors, which are available in many forms, e.g., substantially compact or portable forms. This allows such embodiments to be substantially smaller and lighter than contemporary background oriented Schlieren devices.

With particular reference to FIG. 3, a block diagram shows a direct display based Schlieren system, according to an example of an embodiment. An imager or imaging camera can be a digital camera 31. A target primary image plane 32 can be an image plane for a wavefront-distorting item of interest or target 311, e.g., the object for which an image or information is desired. A background primary image plane 33 can be formed for the background. A condenser lens 34 can facilitate focusing of the camera 31 upon the primary image plane 33. The cutoff filter 35 can located at the primary image plane 33. Thus, the camera 31 can simultaneously on the background primary image plane 33 and the cutoff filter 35, since the background primary image plane 33 and the cutoff filter 35 can both be in the same plane.

An objective lens 36 can facilitate focusing of the background upon the background primary image plane 33. A Schlieren module enclosure 37 can enclose the camera 31, the condenser lens 34, the cutoff filter 35, and the objective lens 36. The enclosure 37, the camera 31, the condenser lens 34, the cutoff filter 35, and the objective lens 36 can define a receiver module.

A computing device or computer 310 can facilitate control of the digital display 313 and the camera 31. The computer 310 can facilitate control of the cutoff filter 35 for embodiments wherein the cutoff filter 35 is computer controllable. An interface connection 38 can be provided from the computer 310 to the digital camera 31. An interface connection 39 can be provided from the computer 310 to the cutoff filter 35 for embodiments wherein the cutoff filter 35 is computer controllable. An interface connection 312 can be provided from the computer 310 to display device 313.

The background pattern can be produced on the screen of a display device 313 at some distance from the Schlieren receiver module 37, which can be a conventional display device such as a television or computer monitor or a controllable transmissive screen with some other light source such as a flash lamp. The image of the pattern can be collected directly by the receiver module through an objective lens 36 which images the screen image onto the cutoff filter 35 and this filtered image can be routed through the condenser lens 34 and to the camera 31. The camera is normally focused so that a plane between the screen and the device is imaged, producing a focused Schlieren image.

With particular reference to FIG. 4, is a block diagram shows a projector based Schlieren system, according to an example of an embodiment. An imager or imaging camera can be a digital camera 41. A target primary image plane 42 can be an image plane for a wavefront-distorting item of interest or target 411, e.g., the object for which an image or information is desired. A background primary image plane 43 can be formed for the background. A condenser lens 44 can facilitate focusing of the camera 41 upon the primary image plane 43. The cutoff filter 45 can located at the primary image plane 43. Thus, the camera 41 can simultaneously on the background primary image plane 43 and the cutoff filter 45, since the background primary image plane 43 and the cutoff filter 45 can both be in the same plane.

An objective lens 46 can facilitate focusing of the background upon the background primary image plane 43. A Schlieren module enclosure 47 can enclose the camera 41, the condenser lens 44, the cutoff filter 45, and the objective lens 46.

A computing device or computer 410 can facilitate control of the digital display 413 and the camera 41. The computer 410 can facilitate control of the cutoff filter 45 for embodiments wherein the cutoff filter 45 is computer controllable. An interface connection 48 can be provided from the computer 410 to the digital camera 41. An interface connection 49 can be provided from the computer 410 to the cutoff filter 45 for embodiments wherein the cutoff filter 45 is computer controllable.

A single computing device, e.g., the computer 310, 415, can control the digital display 313 or projector 415 and the camera 31, 41, such that a software program operating on the computer 310, 415 can project known images and resulting images can be recorded by the camera 31, 41. This capability allows the point spread function of the digital pixels displayed by the projector to be mapped. If the point spread function of each pixel is inverted and they are then collectively added together, the resulting projection is complementary to the cutoff filter, thus allowing the Schlieren effect to be observed in the camera image.

According to the embodiment of FIG. 4, the background is projected onto a projection screen 418, rather than be provided directly by the digital display 313 of FIG. 3. A projection system 415 can comprise a digital display, such as the digital display 313 of FIG. 3. The projection system 415 can project the background to the projection screen 418 via projection system 415. For example, the projection system 415 can comprise a beam splitter 416 for facilitating such projection. A light baffle 417 can mitigate stray or unused light from the beam splitter 416 to prevent such stray light from interfering with the Schlieren image process, such as by reducing image contrast. An interface connection 414 can be provided from the computer 410 to projection system 415.

In this embodiment, the background pattern is produced on a screen 418 at some distance from the Schlieren receiver module 47. The screen 418 can be a conventional retroreflective screen such as used in film or slide projection, and the image is collected through a beam splitter 416 aligned with the projected beam. Half of the collected light is routed through an objective lens 46 which images the screen image onto the spatial filter (the Schlieren cutoff filter) and this filtered image is usually then routed through a condenser lens and thence to a camera. The camera is normally focused so that a plane between the screen and the device is imaged, producing a focused Schlieren image. A single computing device controls the projector and the camera, such that a software program operating on the computer can project known images and record the resulting images observed by the camera. This capability allows the point spread function of the digital pixels displayed by the projector to be mapped. If the point spread function of each pixel is inverted and they are then collectively added together, the resulting projection is complementary to the cutoff filter, thus allowing the Schlieren effect to be observed in the camera image.

Input to the digital camera 31, 41 can be processed and fed back to the display device 310, 410 in order to generate a Schlieren background pattern which is optimized for the display device or projection device and the optical system. The point spread function of the display pixels can be mapped by displaying a single bright pixel and recording the camera image at each point in the display field or a subset of points which are relevant to the Schlieren function.

The point spread function of the display pixels can be mapped by displaying multiple bright pixels at the same time, recording the camera image at each point in the display field, and then identifying the image of each pixel separately in the software (as shown in FIG. 1 and discussed herein). This requires that the bright pixels have a certain minimum separation or be separable by some property such as color such that the software is capable of distinguishing their images. Such distinction is facilitated if the image of the background is focused on the camera during calibration, since this enables the use of a small pixel separation and thus the measurement for a large number of pixels simultaneously.

An analytical approximation to the optical aberrations, e.g. one known in the art such as, but not limited to, a Zernike polynomial representation or affine map, can first estimated by projecting calibration patterns and that model then used to locate pixels. This allows for a denser spacing of calibration pixels and thus faster calibration.

The camera can be capable of electronically controlled focusing. In this manner, the display screen can be in focus during calibration while the target object may be in focus during Schlieren operation An approximately complimentary grid pattern can be generated without prior calibration. Then the complimentary grid pattern can be perturbed to match the aberrated cutoff grid by an error minimization process of a type which is well known in the art such as simulated annealing.

The effective resolution of the display device can be increased by processing different color components of each pixel separately. The camera image can be processed to improve image features for visualization by image processing techniques which are well known to the state of the art. The Schlieren contrast can be improved by applying an exponential transformation (often called a gamma correction or gamma expansion in the art) relative to the intensity level without Schlieren contrast (i.e. the undistorted background intensity level), rather than relative to a dark background, as is conventional in the art.

The Schlieren module can be firmly attached to the projector or display so as to maintain a stable relationship between the grid image and the cutoff filter. The focal length of the projection system can be matched to the focal length of the main objective in order to provide enhanced sensitivity to wavefront distortions due to passing the same distortion twice at the same angle.

The cutoff filter or grid can be a device with controllable transparency such that the screen grid pattern may be a static, uncontrolled pattern. The calibration software can measure the point spread function with different cutoff grid settings rather than with different display/projector settings.

The cutoff filter can be a device with controllable transparency. The background, e.g., the background grid, can be a controllable display or projection. Thus, the measured Schlieren gradient direction can be controlled dynamically.

The projector or display device can comprise a device with controllable transparency which modulates light from a time-varying light source, such as a flash lamp or other light source. This is useful for, among other things, achieving Schlieren imaging with high time resolution/short exposures.

The point spread function calibration process can accommodate dead pixels in any desired manner. For example, the point spread function calibration process can ignore any dead pixels.

Thus, alignment of the Schlieren imaging system can be substantially simplified. The setup process for Schlieren imaging can consequently be simplified and therefore more quickly and easily accomplished. The use of an electronic display, such as a digital display or digitally controlled display, provides enhanced flexibility with respect to the background used. The background can readily be changed (such as from vertical to horizontal stripes).

Embodiments described above illustrate, but do not limit, the invention. It should also be understood that numerous modifications and variations are possible in accordance with the principles of the present invention. Accordingly, the scope of the invention is defined only by the following claims.

The invention claimed is:

1. A device comprising:
a digital display configured to provide a background for schlieren imaging;
a cutoff filter onto which the background is focused;
a processor configured to control a position of the background to align an image of the background with respect to the cutoff filter to facilitate schlieren imaging; and
a camera configured to image the cutoff filter and the background to facilitate schlieren imaging.

2. The device of claim 1, wherein a direct image of the background is focused upon the cutoff filter.

3. The device of claim 1, wherein a projected image of the background is focused upon the cutoff filter.

4. The device of claim 1, wherein the background is complementary with respect to the cutoff filter.

5. The device of claim 1, wherein the processor is configured to control the position of the background to facilitate alignment of the background with respect to the cutoff filter such that a plurality of filter edges of the cutoff filter lie along a plurality of edges of the background.

6. The device of claim 1, wherein the digital display comprises a light emitting diode (LED) display.

7. The device of claim 1, wherein the digital display comprises a liquid crystal display (LCD).

8. The device of claim 1, wherein the digital display comprises:
a light source; and
an electronically controllable light transmissive screen for selectively allowing light from the light source to be transmitted therethrough.

9. A method comprising:
forming a pixel image on a digital display;
focusing the pixel image on a cutoff filter;
imaging the cutoff filter and the pixel image with a camera; and
varying, using a hardware processor, a position of the pixel image with respect to the cutoff filter to align the pixel image with respect to the cutoff filter to facilitate schlieren imaging.

10. The method of claim 9, wherein varying a position of the pixel image with respect to the cutoff filter comprises moving the pixel image such that a plurality of filter edges of the cutoff filter lie along a plurality of edges of the pixel image.

11. The method of claim 9, further comprising mapping a point spread function of the pixel image with respect to the cutoff filter.

12. The method of claim 9, further comprising:
mapping a point spread function of the pixel image with respect to the cutoff filter; and
wherein the point spread function of the display pixels is mapped by displaying a single pixel and imaging the single pixel with the camera at a plurality of points in a display field.

13. The method of claim 9, further comprising:
mapping a point spread function of the pixel image with respect to the cutoff filter; and
wherein the point spread function of the display pixels is mapped by displaying a plurality of pixels simultaneously and imaging the plurality of pixels with the camera.

14. The method of claim 9, further comprising:
inverting a point spread function of each pixel;
adding the inverted point spread functions together to provide a projection that is complementary to the cutoff filter; and
observing a schlieren effect with the camera.

15. The method of claim 9, further comprising:
processing an output of the camera to provide a feedback signal; and
providing the feedback to the display device to generate an enhanced schlieren background pattern.

16. The method of claim 9, wherein the digital display, the cutoff filter, and the camera are part of a schlieren imaging system that has optical aberrations and further comprising:
estimating an analytical approximation to the optical aberrations by projecting a plurality of calibration patterns to define a model; and
using the model to determine locations of a plurality of pixels for use in mapping a point spread function.

17. The method of claim 9, wherein the digital display, the cutoff filter, and the camera are part of a schlieren imaging system that has optical aberrations and further comprising:
estimating at least one of a Zernike polynomial representation or affine map with respect to optical aberrations by projecting calibration patterns to define a model; and
using the model to determine locations of a plurality of pixels for use in mapping a point spread function.

18. A method comprising:
forming a pixel image on a digital display including generating an approximately complementary grid pattern without a prior calibration;
focusing the pixel image on a cutoff filter;
imaging the cutoff filter and the pixel image with a camera; and
varying a position of the pixel image with respect to the cutoff filter including perturbing the grid pattern to match an aberrated cutoff grid by an error minimization process to align the pixel image with respect to the cutoff filter to facilitate schlieren imaging.

19. The method of claim 9, further comprising enhancing an effective resolution of the digital display by processing different color components of each pixel separately.

20. The method of claim 9, further comprising enhancing a schlieren contrast by applying an exponential transformation relative to an intensity level without schlieren contrast.

21. The method of claim 9, wherein:
the cutoff filter comprises a device with controllable transparency; and
varying a position of the pixel image with respect to the cutoff filter comprises moving a pattern of the cutoff filter.

22. The method of claim 9, wherein:
the cutoff filter comprises a device with controllable transparency; and
the cutoff filter comprises one of a controllable display such that a measured schlieren gradient direction can be controlled dynamically.

23. The method of claim 9, further comprising:
time varying the intensity of light source; and
wherein the digital display has controllable transparency and is configured to modulate light from the time varying light source.

24. A device comprising:
a digital display configured to provide a background for schlieren imaging;
a cutoff filter onto which the background is focused;
a camera configured to image the cutoff filter and the background to facilitate schlieren imaging; and
a processor configured to control a position of the cutoff filter to align an image of the cutoff filter with respect to the background to facilitate schlieren imaging.

* * * * *

UNITED STATES PATENT AND TRADEMARK OFFICE
CERTIFICATE OF CORRECTION

Page 1 of 1

PATENT NO. : 9,232,117 B2
APPLICATION NO. : 13/796237
DATED : January 5, 2016
INVENTOR(S) : Benjamin D. Buckner and Drew L'Esperance It is certified that error appears in the above-identified patent and that said Letters Patent is hereby corrected as shown below:

In column 4, line 31/32:
Change the word "complimentary" to --"complementary"--

In column 5, line 47:
Change the word "complimentary" to --"complementary"--

In column 6, line 2:
Add --"or modulator"--

Column 6, line 2 should read:
--"source or modulator"--

In column 7, line 11:
Change the word "relative" to --"normalized"--

In column 10, line 39:
Change the word "complimentary" to --"complementary"--

In column 10, line 40:
Change the word "complimentary" to --"complementary"--

Signed and Sealed this
Tenth Day of May, 2016

Michelle K. Lee
*Director of the United States Patent and Trademark Office*